United States Patent
Bailey (10) Patent No.: US 10,251,382 B2
(45) Date of Patent: Apr. 9, 2019

(54) WEARABLE DEVICE FOR FISHING

(71) Applicant: NAVICO HOLDING AS, Egersund (NO)

(72) Inventor: Paul Robert Bailey, Ellerslie (NZ)

(73) Assignee: NAVICO HOLDING AS, Egersund (NO)

( * ) Notice: Subject to any disclaimer, the term of this patent is extended or adjusted under 35 U.S.C. 154(b) by 22 days.

(21) Appl. No.: 14/032,319

(22) Filed: Sep. 20, 2013

(65) Prior Publication Data
US 2015/0057968 A1    Feb. 26, 2015

Related U.S. Application Data

(60) Provisional application No. 61/868,444, filed on Aug. 21, 2013.

(51) Int. Cl.
*G01C 9/00* (2006.01)
*G01C 17/00* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 16/9535* (2019.01); *G06K 9/00342* (2013.01); *G06Q 10/00* (2013.01); *G06Q 50/01* (2013.01); *G06T 7/246* (2017.01);
(Continued)

(58) Field of Classification Search
CPC ....................................................... G01B 21/00
USPC .......................................................... 702/150
See application file for complete search history.

(56) References Cited

U.S. PATENT DOCUMENTS

| 4,751,787 A | 6/1988 | Jonsson |
|---|---|---|
| 4,829,493 A | 5/1989 | Bailey |

(Continued)

FOREIGN PATENT DOCUMENTS

| DE | 102004059619 A1 | 6/2006 |
|---|---|---|
| EP | 749687 | * 12/1996 |

(Continued)

OTHER PUBLICATIONS

PCT International Search Report and Written Opinion; PCT/162013/060285; dated Feb. 18, 2014.
(Continued)

*Primary Examiner* — Michael P Nghiem
(74) *Attorney, Agent, or Firm* — Nelson Mullins Riley & Scarborough LLP (57) ABSTRACT

Various implementations described herein are directed to a wearable device used to record fishing data. The wearable device may include a housing. The housing may include a sensor or sensors to detect motion. The housing may include a computer system with a processor and memory. The memory may have a plurality of executable instructions. When the executable instructions are executed by the processor, the processor may receive motion data from the sensor or sensors and determine whether a cast has been made.

24 Claims, 5 Drawing Sheets

(51) Int. Cl.

| | | |
|---|---|---|
| G01C 19/00 | (2013.01) | |
| A01K 97/00 | (2006.01) | |
| H04N 5/232 | (2006.01) | |
| H04N 5/91 | (2006.01) | |
| H04N 21/4335 | (2011.01) | |
| G06F 16/9535 | (2019.01) | |
| G08C 17/02 | (2006.01) | |
| G06F 3/01 | (2006.01) | |
| G06F 3/023 | (2006.01) | |
| G06F 15/02 | (2006.01) | |
| G06T 11/20 | (2006.01) | |
| G06T 7/60 | (2017.01) | |
| G11B 27/031 | (2006.01) | |
| G11B 27/17 | (2006.01) | |
| G11B 31/00 | (2006.01) | |
| A01K 99/00 | (2006.01) | |
| G01C 21/20 | (2006.01) | |
| A61B 5/11 | (2006.01) | |
| G01B 21/00 | (2006.01) | |
| G06Q 10/00 | (2012.01) | |
| G06Q 50/00 | (2012.01) | |
| A01K 79/00 | (2006.01) | |
| G06F 11/34 | (2006.01) | |
| G06K 9/00 | (2006.01) | |
| G11B 27/28 | (2006.01) | |
| G11B 27/34 | (2006.01) | |
| G06F 3/0346 | (2013.01) | |
| H04Q 9/00 | (2006.01) | |
| G06T 7/246 | (2017.01) | |
| G06T 7/292 | (2017.01) | |
| B63B 49/00 | (2006.01) | |
| G01S 15/96 | (2006.01) | |
| G06F 11/30 | (2006.01) | |
| G01S 7/00 | (2006.01) | |

(52) U.S. Cl.
CPC .............. *G06T 7/292* (2017.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02D 10/34* (2018.01)

(56) References Cited

U.S. PATENT DOCUMENTS

| | | | |
|---|---|---|---|
| 4,879,697 A | 11/1989 | Lowrance et al. | |
| 5,025,423 A | 6/1991 | Earp | |
| 5,191,341 A | 3/1993 | Gouard et al. | |
| 5,228,228 A * | 7/1993 | Meissner | A01K 97/125 43/17 |
| 5,321,391 A * | 6/1994 | Fox | 340/573.2 |
| 5,446,775 A * | 8/1995 | Wright et al. | 377/24.2 |
| 5,537,380 A | 7/1996 | Sprankle, Jr. et al. | |
| 5,546,695 A | 8/1996 | Langer | |
| 6,045,076 A | 4/2000 | Daniels | |
| 6,125,571 A * | 10/2000 | Sigwald | A01K 97/125 43/16 |
| 6,222,449 B1 | 4/2001 | Twining | |
| 6,225,984 B1 | 5/2001 | Crawford | |
| 6,252,544 B1 * | 6/2001 | Hoffberg | 342/357.31 |
| 6,263,147 B1 | 7/2001 | Tognazzini | |
| 6,321,158 B1 | 11/2001 | DeLorme et al. | |
| 6,411,283 B1 | 6/2002 | Murphy | |
| 6,418,080 B2 | 7/2002 | Inouchi | |
| 6,421,299 B1 | 7/2002 | Betts et al. | |
| 6,567,792 B1 * | 5/2003 | Arnold | A01K 79/00 43/54.1 |
| 6,584,722 B1 * | 7/2003 | Walls | A01K 97/00 377/5 |
| 6,587,740 B2 | 7/2003 | Byrne et al. | |
| 6,761,692 B2 | 7/2004 | Angelsen et al. | |
| 6,798,378 B1 | 9/2004 | Walters | |
| 6,816,782 B1 | 11/2004 | Walters et al. | |
| 7,002,579 B2 | 2/2006 | Olson | |
| 7,236,426 B2 | 6/2007 | Turner et al. | |
| 7,243,457 B1 | 7/2007 | Smith et al. | |
| 7,319,992 B2 | 1/2008 | Gaos | |
| 7,430,461 B1 | 9/2008 | Michaels | |
| 7,652,952 B2 | 1/2010 | Betts et al. | |
| 7,669,360 B2 | 3/2010 | Davidson | |
| 7,710,825 B2 | 5/2010 | Betts et al. | |
| 7,722,218 B2 | 5/2010 | Leung | |
| 7,729,203 B2 | 6/2010 | Betts et al. | |
| 7,755,974 B2 | 7/2010 | Betts et al. | |
| 7,812,667 B2 | 10/2010 | Fagg | |
| 7,870,496 B1 | 1/2011 | Sherwani | |
| 7,890,867 B1 | 2/2011 | Margulis | |
| 8,019,532 B2 | 9/2011 | Sheha et al. | |
| 8,040,758 B1 | 10/2011 | Dickinson | |
| 8,063,540 B2 | 11/2011 | Angelsen et al. | |
| 8,082,100 B2 | 12/2011 | Grace et al. | |
| 8,364,806 B2 | 1/2013 | Short et al. | |
| 8,452,797 B1 | 5/2013 | Paleja et al. | |
| 8,468,164 B1 | 6/2013 | Paleja et al. | |
| 8,512,238 B2 | 8/2013 | Nissilä et al. | |
| 8,721,453 B2 | 5/2014 | Rosing | |
| 9,439,411 B2 | 9/2016 | Bailey | |
| 9,507,562 B2 * | 11/2016 | Bailey | G06F 3/167 |
| 9,572,335 B2 * | 2/2017 | Bailey | G08C 17/02 |
| 9,615,562 B2 * | 4/2017 | Bailey | G11B 27/17 |
| 2001/0054961 A1 | 12/2001 | Twining | |
| 2002/0035574 A1 | 3/2002 | Dumas | |
| 2002/0093541 A1 | 7/2002 | Schileru-Key | |
| 2002/0099457 A1 | 7/2002 | Fredlund et al. | |
| 2002/0116421 A1 | 8/2002 | Fox et al. | |
| 2003/0046689 A1 | 3/2003 | Gaos | |
| 2003/0056419 A1 | 3/2003 | Squires et al. | |
| 2003/0089020 A1 | 5/2003 | Dirito | |
| 2003/0147981 A1 | 8/2003 | Gillam | |
| 2004/0124297 A1 * | 7/2004 | Steer | 242/223 |
| 2004/0162830 A1 | 8/2004 | Shirwadkar et al. | |
| 2004/0193364 A1 | 9/2004 | Chojnacki | |
| 2004/0198554 A1 | 10/2004 | Orr et al. | |
| 2004/0249860 A1 | 12/2004 | Stechschulte et al. | |
| 2005/0011105 A1 * | 1/2005 | Cameron | A01K 97/125 43/17 |
| 2005/0037872 A1 | 2/2005 | Fredlund et al. | |
| 2005/0102101 A1 | 5/2005 | Beesley et al. | |
| 2006/0013066 A1 | 1/2006 | Nishimori et al. | |
| 2006/0048434 A1 | 3/2006 | Congel | |
| 2006/0095393 A1 | 5/2006 | Vinsant | |
| 2006/0119585 A1 | 6/2006 | Skinner | |
| 2006/0224940 A1 | 10/2006 | Lee | |
| 2006/0265931 A1 | 11/2006 | McFadden et al. | |
| 2007/0011334 A1 | 1/2007 | Higgins et al. | |
| 2007/0045010 A1 | 3/2007 | Kasperek | |
| 2007/0058489 A1 | 3/2007 | Bratcher | |
| 2007/0220798 A1 * | 9/2007 | Davidson | 43/4 |
| 2008/0126935 A1 | 5/2008 | Blomgren | |
| 2008/0165022 A1 | 7/2008 | Herz et al. | |
| 2008/0204424 A1 | 8/2008 | Jin et al. | |
| 2008/0246627 A1 | 10/2008 | Guazzelli | |
| 2009/0064055 A1 | 3/2009 | Chaudhri et al. | |
| 2009/0099871 A1 | 4/2009 | Gadodia | |
| 2009/0105952 A1 | 4/2009 | Grace et al. | |
| 2009/0179789 A1 | 7/2009 | Haughay, Jr. et al. | |
| 2009/0231190 A1 | 9/2009 | Grumbles | |

(56) References Cited

U.S. PATENT DOCUMENTS

| | | |
|---|---|---|
| 2009/0240354 A1 | 9/2009 | Davidson |
| 2009/0241636 A1 | 10/2009 | Obori |
| 2009/0249247 A1 | 10/2009 | Tseng et al. |
| 2009/0258710 A1 | 10/2009 | Quatrochi |
| 2009/0271054 A1 | 10/2009 | Dokken |
| 2009/0287409 A1 | 11/2009 | Summers |
| 2009/0293336 A1 | 12/2009 | Lankinen |
| 2009/0295626 A1 | 12/2009 | Su |
| 2010/0049468 A1* | 2/2010 | Papadourakis ............ 702/141 |
| 2010/0080082 A1 | 4/2010 | Betts et al. |
| 2010/0121716 A1 | 5/2010 | Golan |
| 2010/0145601 A1 | 6/2010 | Kurtti et al. |
| 2010/0198650 A1 | 8/2010 | Shaw |
| 2010/0199225 A1 | 8/2010 | Coleman et al. |
| 2010/0226203 A1 | 9/2010 | Buttle et al. |
| 2010/0250122 A1 | 9/2010 | Kubota et al. |
| 2010/0295781 A1 | 11/2010 | Alameh et al. |
| 2010/0319235 A1 | 12/2010 | Panaro |
| 2011/0007035 A1 | 1/2011 | Shai |
| 2011/0013484 A1 | 1/2011 | Coleman et al. |
| 2011/0013485 A1 | 1/2011 | Maguire |
| 2011/0019887 A1 | 1/2011 | Roehrig et al. |
| 2011/0025720 A1 | 2/2011 | Jo et al. |
| 2011/0067290 A1* | 3/2011 | Miskatovic .......... A01K 97/125 43/17 |
| 2011/0082644 A1 | 4/2011 | Imasaka et al. |
| 2011/0154183 A1 | 6/2011 | Burns et al. |
| 2011/0208479 A1 | 8/2011 | Chaves |
| 2011/0213515 A1 | 9/2011 | Haymart et al. |
| 2011/0214500 A1 | 9/2011 | Cabrera et al. |
| 2011/0257819 A1 | 10/2011 | Chen et al. |
| 2012/0001773 A1 | 1/2012 | Lyons et al. |
| 2012/0010478 A1 | 1/2012 | Kinnunen et al. |
| 2012/0011437 A1 | 1/2012 | James et al. |
| 2012/0014220 A1 | 1/2012 | DePasqua |
| 2012/0047790 A1 | 3/2012 | Hess et al. |
| 2012/0069712 A1 | 3/2012 | Potanin et al. |
| 2012/0095978 A1 | 4/2012 | Levin et al. |
| 2012/0106300 A1 | 5/2012 | Maguire |
| 2012/0144384 A1 | 6/2012 | Back |
| 2012/0144723 A1 | 6/2012 | Davidson |
| 2012/0185801 A1 | 7/2012 | Madonna et al. |
| 2012/0253485 A1 | 10/2012 | Weast et al. |
| 2012/0293323 A1 | 11/2012 | Kalb et al. |
| 2012/0316456 A1 | 12/2012 | Rahman et al. |
| 2012/0316458 A1 | 12/2012 | Rahman et al. |
| 2012/0317167 A1 | 12/2012 | Rahman et al. |
| 2013/0007665 A1 | 1/2013 | Chaudhri et al. |
| 2013/0040714 A1* | 2/2013 | Rosing .................... A63F 13/65 463/7 |
| 2013/0074051 A1 | 3/2013 | Freeman |
| 2013/0096575 A1 | 4/2013 | Olson |
| 2013/0107031 A1 | 5/2013 | Atkinson |
| 2013/0109997 A1 | 5/2013 | Linke et al. |
| 2013/0271301 A1 | 10/2013 | Kabel et al. |
| 2013/0281087 A1 | 10/2013 | Ruhanen et al. |
| 2014/0012587 A1 | 1/2014 | Park |
| 2014/0032468 A1 | 1/2014 | Anandaraj |
| 2014/0071059 A1 | 3/2014 | Girault |
| 2014/0111368 A1 | 4/2014 | Lee et al. |
| 2014/0135592 A1 | 5/2014 | Ohnemus et al. |
| 2014/0135631 A1 | 5/2014 | Brumbaek et al. |
| 2014/0180566 A1 | 6/2014 | Malhotra |
| 2014/0195297 A1 | 7/2014 | Abuelsaad et al. |
| 2014/0221854 A1 | 8/2014 | Wai |
| 2014/0358483 A1 | 12/2014 | da Rosa |
| 2015/0019135 A1 | 1/2015 | Kacyvenski |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1* | 2/2015 | Gaynor .................. G08C 17/02 702/141 |
| 2015/0057968 A1 | 2/2015 | Bailey |
| 2015/0058020 A1* | 2/2015 | Bailey ........................ 704/275 |
| 2015/0058237 A1 | 2/2015 | Bailey |
| 2015/0058323 A1 | 2/2015 | Bailey |
| 2015/0245777 A1 | 9/2015 | Della Tone et al. |
| 2015/0310524 A1 | 10/2015 | Gospodarek et al. |
| 2015/0313199 A1 | 11/2015 | Castaneda et al. |
| 2015/0342481 A1 | 12/2015 | Lie et al. |
| 2016/0125348 A1 | 5/2016 | Dyer et al. |

FOREIGN PATENT DOCUMENTS

| | | | |
|---|---|---|---|
| EP | 1 561 377 A1 | | 8/2005 |
| EP | 1782687 | | 5/2007 |
| EP | 2356902 | * | 8/2011 |
| EP | 2 613 223 A1 | | 7/2013 |
| GB | 2244195 | * | 11/1991 |
| GB | 2426680 | * | 12/2006 |
| GB | 2470904 | | 12/2010 |
| JP | 2004 207812 A | | 7/2004 |
| JP | 2006 158239 A | | 6/2006 |
| JP | 2010 193284 A | | 9/2010 |
| JP | 2011 139647 A | | 7/2011 |
| WO | WO 98/02037 A1 | | 1/1998 |
| WO | WO 2004/088572 A1 | | 10/2004 |
| WO | WO 2010/056392 A1 | | 5/2010 |
| WO | WO2012059734 | * | 5/2012 |
| WO | WO 2012/170163 A1 | | 12/2012 |
| WO | WO 2014/088508 A1 | | 6/2014 |
| ZA | 200 308 052 A | | 7/2004 |

OTHER PUBLICATIONS

PCT International Search Report and Written Opinion; PCT/US2013/047869; dated Oct. 21, 2013.

PCT International Search Report and Written Opinion; PCT/US2013/048177; dated Oct. 21, 2013.

PCT International Search Report and Written Opinion; PCT/US2013/048129; dated Oct. 17, 2013.

PCT International Search Report and Written Opinion; PCT/US2013/047926; dated Oct. 11, 2013.

PCT International Search Report and Written Opinion; PCT/US2013/047645; dated Sep. 27, 2013.

First look at new Mio Link ANT +/Bluetooth Smart optical heart rate wrist band; http://www.dcrainmaker.com/2014/01/mio-link-first-look.html; Jan. 6, 2014 (accessed Apr. 18, 2016).

SAS, "SAS BI Dashboard 4.31 User's Guide", Second Edition, by SAS Electronic book, Aug. 1, 2012, downloaded at http://support.sas.com/documentation/cdl/en/bidbrdug/65580/PDF/default/bidrdrug.pdf.

PCT International Search Report and Written Opinion; PCT/I62014/063973, dated Nov. 28, 2014; all enclosed pages cited.

PCT International Search Report and Written Opinion; PCT/I62014/063981, dated Feb. 10, 2015; all enclosed pages cited.

PCT International Search Report and Written Opinion; PCT/I62014/063978, dated Dec. 19, 2014; all enclosed pages cited.

PCT International Search Report and Written Opinion; PCT/I62014/063977, dated Nov. 28, 2014; all enclosed pages cited.

Allen, et al.; Upper Extremity Kinematic Trends of Fly-Casting; Establishing the Effects of Line Length; Sports Biomechanics; vol. 7, No. 1; Jan. 1, 2008; pp. 38-53.

PCT International Search Report and Written Opinion; PCT/IB2014/063974, dated Dec. 2, 2014.

PCT International Search Report and Written Opinion; PCT/IB2014/063975, dated Dec. 3, 2014.

PCT International Search Report and Written Opinion; PCT/IB2014/063976, dated Dec. 12, 2014.

PCT International Search Report and Written Opinion; PCT/IB2014/063979, dated Jan. 7, 2015.

PCT International Search Report and Written Opinion; PCT/IB2014/063980, dated Jan. 5, 2015.

(56) References Cited

OTHER PUBLICATIONS

PCT International Search Report and Written Opinion; PCT/IB2014/063982, dated Dec. 22, 2014.
PCT International Search Report and Written Opinion; PCT/IB2014/063983, dated Mar. 5, 2015.
McElderry; At-Sea Observing Using Video-Based Electronic Monitoring; Prepared for: Electronic Monitoring Workshop Jul. 29-30, 2008; Archipelago Marine Research Ltd.
Office Action Issued in Canadian Patent Application 2,921,317, dated Feb. 7, 2017.
Cristando et al. "Nikeplus Ecosystem Strategy" retrieved Sep. 1, 2017 from <http://studylib.net/doc/8718940/nikeplus-ecosystem-strategy> 12 pages.
Joey Davidson, "Jaybird Reign REVIEW—Lightweight, simple, lacking" Feb. 28, 2016, Technobuffalo, retrieved Sep. 1, 2017 from <https://www.technobuffalo.com/reviews/jaybird-reign-review/> 14 pages.

* cited by examiner

Fishing Motion Detection Software  300

WEARABLE DEVICE FOR FISHING

CROSS-REFERENCE TO RELATED APPLICATIONS

This application claims the benefit of U.S. Provisional Patent Application Ser. No. 61/868,444, filed Aug. 21, 2013 titled FISHING DATA COLLECTION AND USE, and the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Accurate data, including, for example, a count of fishing casts made, can be very useful for a fisherman. A device that can capture this data can provide advantages to a fisherman. Such advantages include requiring less time to record information, and collecting more accurate data.

SUMMARY

Described herein are implementations of various technologies for an apparatus for recording fishing data. The apparatus is a wearable device. The apparatus includes a housing. The housing includes a sensor or sensors to detect motion. The housing includes a computer system with a processor and memory. The memory has a plurality of executable instructions. In one implementation, when the executable instructions are executed by the processor, the processor may receive motion data from the sensor or sensors and determine whether a fishing cast has been made.

Described herein are also implementations of various technologies for a method for recording motion data corresponding to a fishing cast. In one implementation, a non-transitory computer-readable medium having stored thereon computer-executable instructions which, when executed by a computer, cause the computer to perform various actions. The actions may include receiving motion data from a sensor or sensors. The received motion data may be analyzed to determine whether a cast has been made. If a cast has been made, the occurrence of the cast and the time of the cast may then be recorded.

Described herein are also implementations of various technologies for a method for recording motion data corresponding to a fish bite or a caught fish. In one implementation, a non-transitory computer-readable medium having stored thereon computer-executable instructions which, when executed by a computer, cause the computer to perform various actions. The actions may include receiving motion data from a sensor or sensors. In one implementation, the received motion data may be analyzed to determine whether a bite or catch has occurred. If a catch or bite has occurred, the occurrence of the catch or bite and the time of the catch or bite may then be recorded.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of a wearable device described herein will now be described in more detail with reference to FIGS. 1-6.

Wearable Device for Fishing

Figure 1:
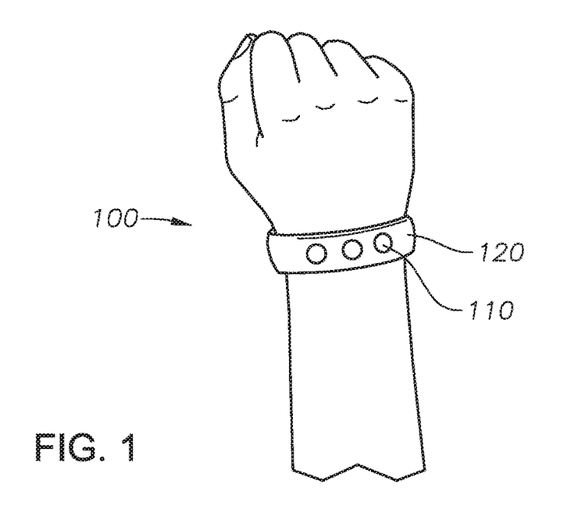
FIG. 1 illustrates a wearable device in accordance with implementations of various techniques described herein.

Fishermen often record details of their fishing trips so that the information can be referenced at a later time, and so that the trip can be analyzed. Using a wearable device that captures motion and determines when a cast has been made, fishing data could easily be recorded by a computer system without the need for significant user input. Accordingly, FIG. 1 illustrates a wearable device 100 in accordance with various implementations described herein. The wearable device 100 may be worn around the fisherman's arm or wrist. The wearable device 100 could also be attached to a fishing rod.

The wearable device 100 may include a housing 120. In one implementation, the housing 120 may be in the shape of a band. The housing 120 may be made of a combination of plastics and rubbers, or of any other synthetic material. The housing 120 may also be waterproof. The housing 120 may include a clasp, or another mechanism to aid in removal of the housing 120 from a user's arm.

Figure 2:
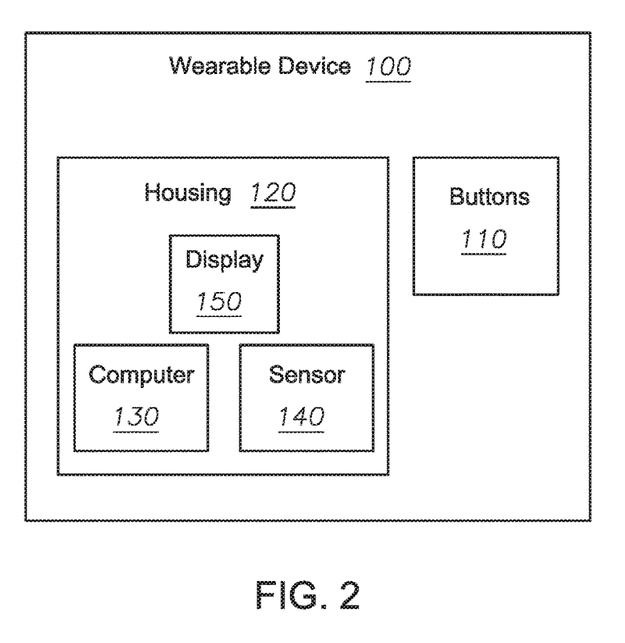
FIG. 2 is a block diagram of a wearable device in accordance with implementations of various techniques described herein.

FIG. 2 illustrates a block diagram of the wearable device 100 in accordance with various implementations described herein. As shown in FIG. 2, the housing 120 may include a computer 130 and at least one motion sensor 140. The at least one motion sensor 140 may include one or more accelerometers, gyroscopes, muscle activity sensors, any other motion sensor, or any combination of motion sensors. The at least one motion sensor 140 is configured to capture motion data.

Figure 5:
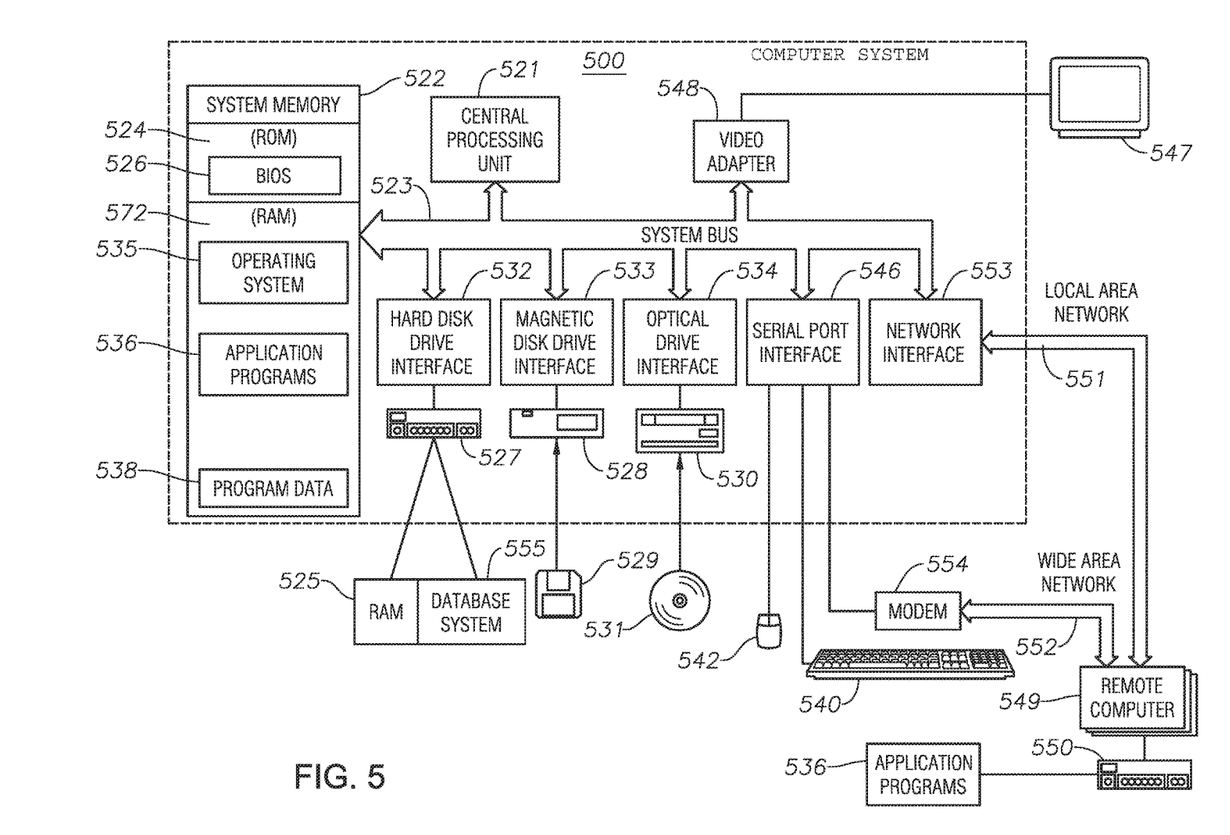
FIG. 5 illustrates a schematic diagram of a computing system in which the various technologies described herein may be incorporated and practiced.

The computer 130 is described in more detail in FIG. 5. In one implementation, the computer 130 may be loaded with software to analyze motion data from the at least one motion sensor 140. For instance, the software may analyze motion data to determine when a fishing cast motion has been made. The software may also record that a cast has been made and the time of the cast, e.g., a timestamp. The software is described in more detail in FIG. 3.

The wearable device 100 may include one or more buttons 110. The one or more buttons 110 may be used for user input. In one implementation, the one or more buttons 110 may be used to input the occurrence of a catch. The catch may then be recorded. In another implementation, the one or more buttons 110 may be used to input the weight of a caught fish. The weight may then be recorded. In yet another implementation, a user may press a button 110 to input the occurrence of a catch, and then may press the same or different button 110 to input the weight of the caught fish. The occurrence of the catch and the weight may then be recorded. In still another implementation, the one or more buttons 110 may be used to input the occurrence of a bite.

The wearable device may contain a display 150. The display may be a series of Light Emitting Diodes (LED). The display may be a Liquid Crystal Display (LCD).

The wearable device 100 may include wireless technology, such as Bluetooth, Wi-Fi, cellular technology such as GSM or CDMA, satellite communication, or any other wireless technology. In one implementation, the wearable device 100 may be connected wirelessly to a marine electronics device 600, which is described in more detail in FIG. 6. Although the wearable device 100 is described as being wirelessly connected to a marine electronics device 600, it should be understood that the wearable device 100 may be connected to any computer system, including a portable computer system, a smart phone device, a remote server, a cloud server and the like. It should also be understood that the wearable device 100 may be connected to any other device able to store fishing data, e.g., data logging device.

Figure 6:
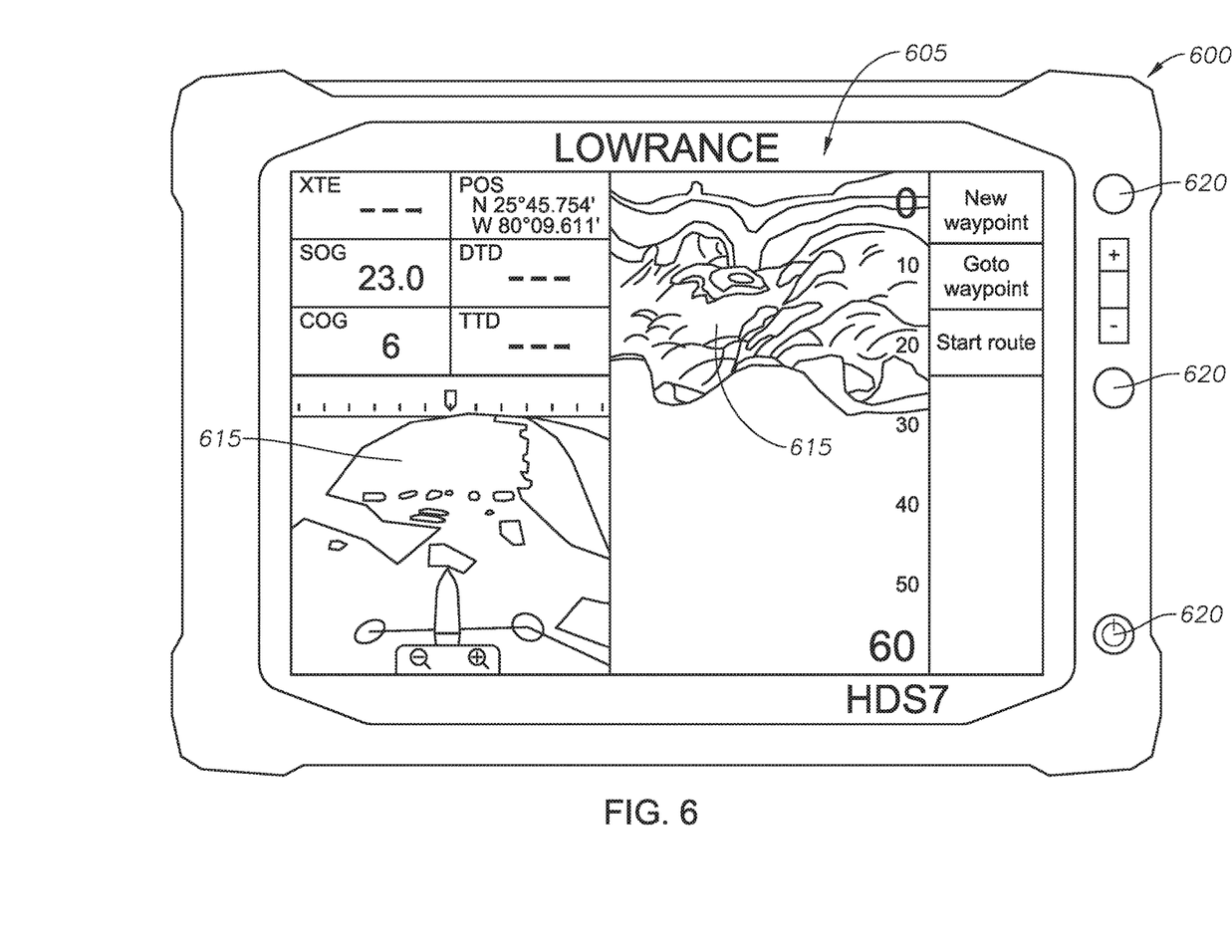
FIG. 6 illustrates a schematic of a marine electronics device in accordance with implementations of various techniques described herein.

The marine electronics device 600 or a computer system, including a smart phone, may record additional data, such as location, weather, or other data. The data from the marine electronics device 600 or computer system and the wearable device 100 may then be combined to provide comprehensive data regarding a fishing trip. The combined data may then be transmitted to a remote server or cloud. In one implementation, the combined data may be transmitted to a smart phone device, which then transmits the data to a remote server or cloud. In another implementation, the combined data may be transmitted to the data logging device, which may then transmit the combined data at a later time. In yet another implementation, the data from the wearable device 100 may be transmitted to the remote server or cloud via the smart phone without using the marine electronics device 600. In still another implementation, the data from the wearable device may be transmitted to a data logging device prior to being transmitted to a remote server or cloud via the smart phone.

Fishing Motion Detection

Figure 3:
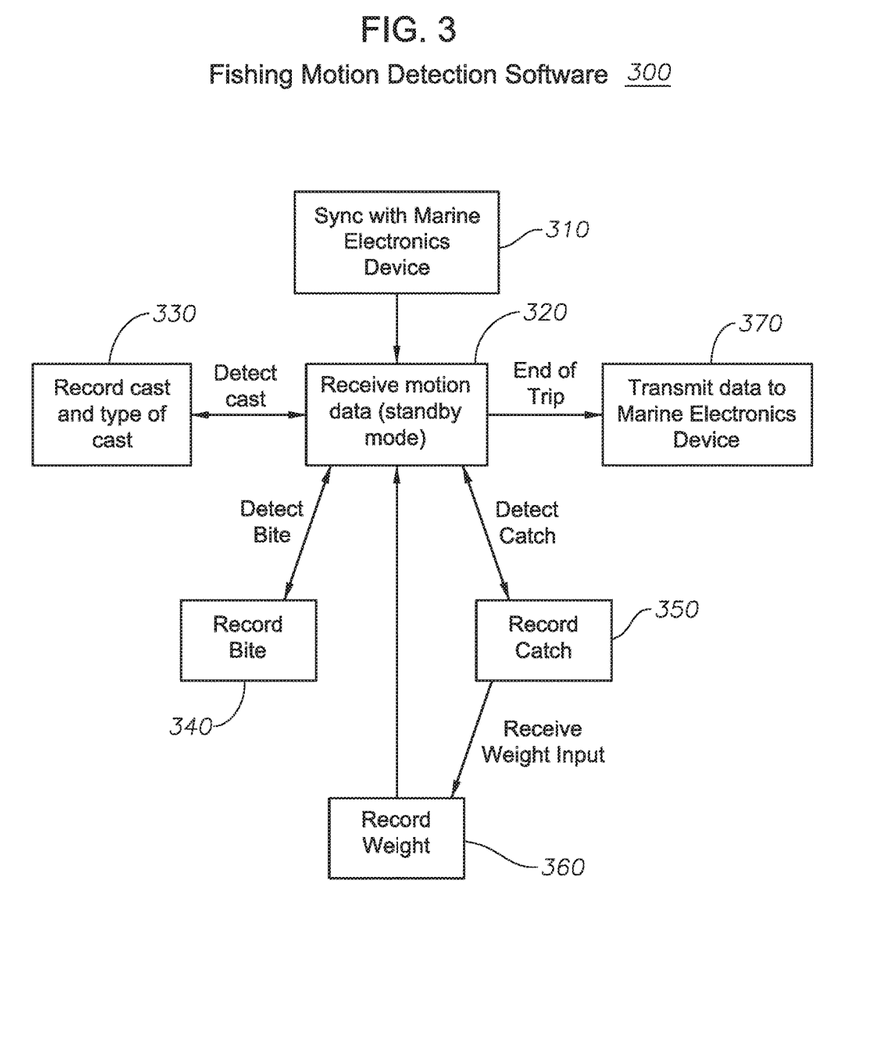
FIG. 3 is a flow diagram describing the operation of a fishing motion detecting software loaded in a wearable device in accordance with implementations of various techniques described herein.

FIG. 3 illustrates a flow diagram of a cast detection method 300 in accordance with implementations of various techniques described herein. In one implementation, method 300 may be performed by the computer 130. It should be understood that while method 300 indicates a particular order of execution of operations, in some implementations, certain portions of the operations might be executed in a different order. Further, in some implementations, additional operations or steps may be added to the method 300. Likewise, some operations or steps may be omitted.

As mentioned above, the computer 130 contained in a wearable device 100 may be loaded with a set of instructions (software) to analyze data received from one or more sensors. The software may receive motion data from the at least one motion sensor 140 in the wearable device. The software may analyze the motion data and determine when a cast has been made. The software may record the occurrence of the cast and time of the cast, e.g., a timestamp in memory, e.g., inside the computer 130. The record may be a database, a log, or any other method of recording the fishing data. The record may be a number representing the amount of casts that have occurred, with the number being incremented after each cast. The amount of casts may be shown on a display 150.

Figure 4:
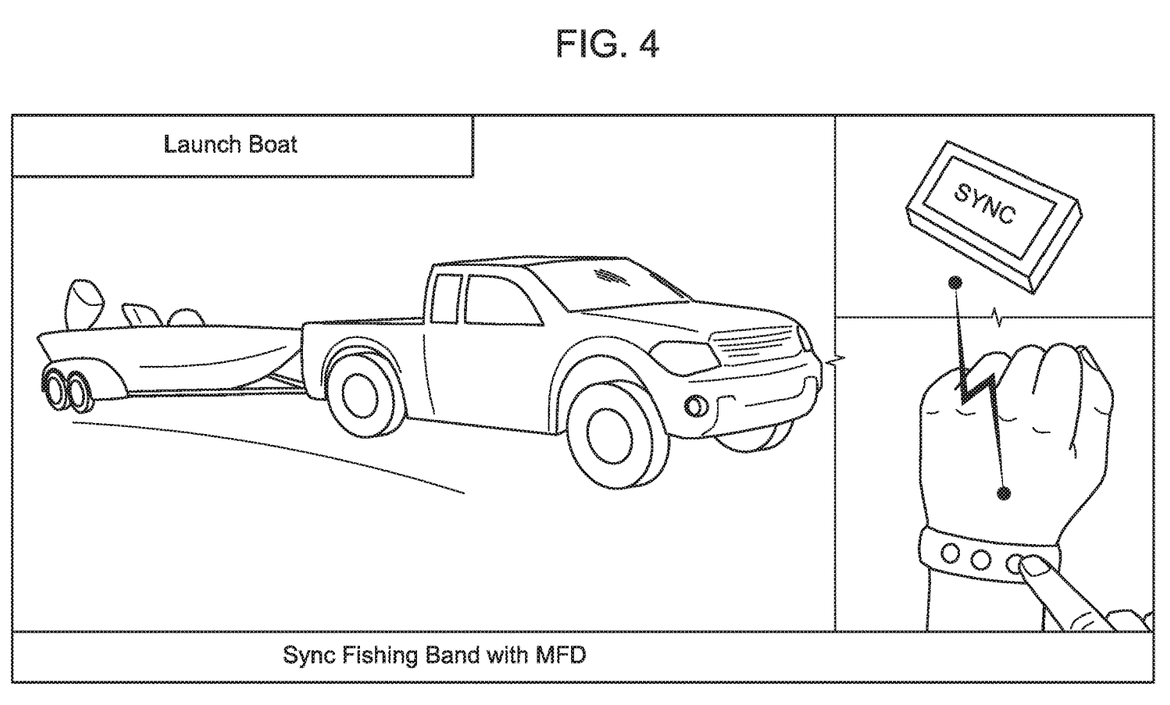
FIG. 4 is an illustration of a wearable device wirelessly transmitting data to a marine electronics device and receiving data from the device in order to begin recording data in accordance with implementations of various techniques described herein.

At block 310, the computer 130 may be synchronized to a marine electronics device or a portable computer device, such as a smart phone. This step is optional. In one implementation, the computer 130 may be wirelessly synchronized to the marine electronics device 600. FIG. 4 illustrates the wearable device 100 being synchronized to the marine electronics device.

At block 320, the software may enter a standby mode in which data may be received from the at least one motion sensor 140 and analyzed. At this step, the software may continuously monitor for a cast. Once a cast is detected, the cast and the timestamp corresponding to the detected cast may be recorded (block 330). In one implementation, the software may determine the type of cast used using motion sensor data (block 330). The software may determine whether the cast made is a basic cast, roll cast, side cast, or any other type of cast. The software may then record the type of cast made (block 330). Then, the software returns to the standby mode (block 310).

While in standby mode (block 310), the software may detect a catch or a bite. The software may detect a catch or a bite based on the motion sensor data. Once a bite or a catch is detected, the occurrence of a bite or a catch and their corresponding timestamp may be recorded (block 340/350). The record may be a database, a log, or any other method of recording the fishing data. The record may be a number representing the amount of bites or catch that have occurred, with the number being incremented after each bite or catch. The amount of bites or catch may be shown on a display 150. Then, the software returns to the standby mode (block 320).

In one implementation, the bites and catches may be detected using one or more buttons 110. To indicate a bite, a user may press a first button 110. To indicate a catch, a user may press a second, different button 110. Alternately, a user may press a button 110 and then quickly release the button 110 to indicate the occurrence of a bite. The user may also press the same button 110 and hold the button 110 down for a longer time to indicate a catch.

Once a catch is detected, the software may receive further user input corresponding to the weight of the caught fish (block 360). If the software receives further user input, the software may then record the weight of the caught fish (block 360). The record may be a database, a log, or any other method of recording the fishing data. The inputted weight may be shown on a display 150. Then, the software returns to the standby mode (block 320).

In one implementation, the weight is entered using one or more buttons 110. A weight may be entered by pushing the one or more buttons 110 a number of times to correspond to the weight of the caught fish. For example, to enter a three pound fish, a button 110 may be pressed three times.

When the trip is over, the software may transmit the recorded data wirelessly to the connected device, e.g., the marine electronics device 600 (block 370). In one implementation, the software may transmit the record data after each new entry, or at any other interval. For example, the transmission may be made after each cast. The transmission may be to a remote server or to any computer system, including a smart phone or a marine electronics device.

Marine Electronics Device

FIG. 6 illustrates a schematic diagram of a marine electronics device 600 in accordance with various implementations described herein. The marine electronics device 600 includes a screen 605. In certain implementations, the screen 605 may be sensitive to touching by a finger. In other implementations, the screen 605 may be sensitive to the body heat from the finger, a stylus, or responsive to a mouse. The display device 600 may display marine electronic data 615. The marine electronic data types 615 may include chart data, radar data, sonar data, steering data, dashboard data, navigation data, fishing statistics, and the like. The marine electronics device 600 may also include a plurality of buttons 620, which may be either physical buttons or virtual buttons, or a combination thereof. The contents of the marine display device 600 are described in more detail with reference to FIG. 5.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

FIG. 5 illustrates a computer system 500 into which implementations of various technologies and techniques described herein may be implemented. Computing system 700 may be a conventional desktop, a handheld device, a wearable device, a controller, a personal digital assistant, a server computer, an electronic device/instrument, a laptop, a tablet, or part of a navigation system, marine electronics, or sonar system. It should be noted, however, that other computer system configurations may be used.

The computing system 500 may include a central processing unit (CPU) 521, a system memory 522 and a system bus 523 that couples various system components including the system memory 522 to the CPU 521. Although only one CPU is illustrated in FIG. 5, it should be understood that in some implementations the computing system 500 may include more than one CPU. The system bus 523 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 522 may include a read only memory (ROM) 524 and a random access memory (RAM) 525. A basic input/output system (BIOS) 526, containing the basic routines that help transfer information between elements within the computing system 500, such as during start-up, may be stored in the ROM 524. The computing system may be implemented using a printed circuit board containing various components including processing units, data storage memory, and connectors.

The computing system 500 may further include a hard disk drive 527 for reading from and writing to a hard disk, a magnetic disk drive 528 for reading from and writing to a removable magnetic disk 529, and an optical disk drive 530 for reading from and writing to a removable optical disk 531, such as a CD ROM or other optical media. The hard disk drive 527, the magnetic disk drive 528, and the optical disk drive 530 may be connected to the system bus 523 by a hard disk drive interface 532, a magnetic disk drive interface 533, and an optical drive interface 534, respectively. The drives and their associated computer-readable media may provide nonvolatile storage of computer-readable instructions, data structures, program modules and other data for the computing system 500.

Although the computing system 500 is described herein as having a hard disk, a removable magnetic disk 529 and a removable optical disk 531, it should be appreciated by those skilled in the art that the computing system 500 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 500. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on the hard disk 527, magnetic disk 529, optical disk 531, ROM 524 or RAM 525, including an operating system 535, one or more application programs 536, program data 538, and a database system 555. The operating system 535 may be any suitable operating system that may control the operation of a networked personal or server computer, such as Windows® XP, Mac OS® X, Unix-variants (e.g., Linux® and BSD®), and the like.

A user may enter commands and information into the computing system 500 through input devices such as a keyboard 540 and pointing device 542. Other input devices may include a microphone, joystick, game pad, satellite dish, scanner, user input button, or the like. These and other input devices may be connected to the CPU 521 through a serial port interface 546 coupled to system bus 523, but may be connected by other interfaces, such as a parallel port, game port or a universal serial bus (USB). A monitor 547 or other type of display device may also be connected to system bus 523 via an interface, such as a video adapter 548. In addition to the monitor 547, the computing system 500 may further include other peripheral output devices such as speakers and printers.

Further, the computing system 500 may operate in a networked environment using logical connections to one or more remote computers 549. The logical connections may be any connection that is commonplace in offices, enterprise-wide computer networks, intranets, and the Internet, such as local area network (LAN) 551 and a wide area network (WAN) 552. The remote computers 549 may each include application programs 536 similar to that as described above. The computing system 500 may use a Bluetooth radio to wirelessly communicate with another device.

When using a LAN networking environment, the computing system 500 may be connected to the local network 551 through a network interface or adapter 553. When used in a WAN networking environment, the computing system 500 may include a modem 554, wireless router or other means for establishing communication over a wide area network 552, such as the Internet. The modem 554, which may be internal or external, may be connected to the system bus 523 via the serial port interface 546. In a networked environment, program modules depicted relative to the computing system 500, or portions thereof, may be stored in a remote memory storage device 550. It will be appreciated that the network connections shown are exemplary and other means of establishing a communications link between the computers may be used.

While the foregoing is directed to implementations of various techniques described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A wearable device configured to be attached to an object used for fishing activities, the wearable device comprising:
   a housing having:
      at least one sensor configured to detect motion of the object, wherein the object is an appendage of a user such that motion of the object during the fishing activities defines one or more determinable patterns that are each associated with a corresponding fishing activity, wherein the wearable device is configured to attach to the appendage of the user, wherein the at least one sensor is within the wearable device and not configured to directly attach to the appendage of the user, and wherein the wearable device and the at least one sensor are each not configured to attach to or interact with a fishing line; and
   a computer system having a processor and memory having stored thereon a plurality of executable instructions which, when executed by the processor, cause the processor to:
      receive motion data of the object from the at least one sensor;
      analyze the motion data of the object to determine if the motion of the object defines at least one of the determinable patterns associated with a corresponding fishing activity, wherein the fishing activity includes at least one of occurrence of a cast, occurrence of a bite, or occurrence of a catch;
      determine, based on the motion data from the at least one sensor, that the motion of the object defines at least one of the determinable patterns that corresponds to either the occurrence of a bite or occurrence of a catch, wherein the determinable patterns that correspond to either the occurrence of a bite or occurrence of a catch include motion data that is based on motion of the appendage of the user and not direct motion of the fishing line;
      determine a time associated with receipt of the motion data;
      record the occurrence of the bite or the catch such that the determined time is associated with the occurrence of the bite or the catch; and
      wirelessly transmit the record of the associated occurrence of the bite or the catch and time to a remote marine electronics device for further association with additional data, wherein the additional data includes a location that is recorded by the marine electronics device, and whereby the record of the occurrence of the bite or the catch, the time, and the location are stored in an associated manner in memory of the marine electronics device for operation by the marine electronics device that comprises combination with other fishing data by the marine electronics device to provide comprehensive fishing data of a fishing trip and display by a screen of the marine electronics device.

2. The wearable device of claim 1, wherein the memory further comprises executable instructions which, when executed by the processor, cause the processor to:
   determine an occurrence of a cast in an instance in which the motion of the object defines at least one determinable pattern that corresponds to the occurrence of the cast;
   record the occurrence of the cast such that the determined time is associated with the occurrence of the cast; and
   wirelessly transmit the record of the associated cast and time to the remote marine electronics device for further association with the additional data.

3. The wearable device of claim 1, further comprising at least one user input button configured to record weight information.

4. The wearable device of claim 1, further comprising at least one user input button configured to record at least one of a catch, a timestamp corresponding to the catch, a bite, or weight information corresponding to the catch.

5. The wearable device of claim 1, wherein the housing further comprises a display for displaying information pertaining to the fishing activity that has occurred.

6. The wearable device of claim 1, wherein the at least one sensor comprises at least one of at least one accelerometer, at least one gyroscope sensor, or at least one muscle activity sensor.

7. The wearable device of claim 1, wherein the housing is composed of at least one of a plastic or a rubber.

8. The wearable device of claim 1, wherein the memory further comprises executable instructions which, when executed by the processor, cause the processor to determine a type of fishing cast and record the type of fishing cast based on the motion data.

9. The wearable device of claim 1, wherein the memory further comprises executable instructions which, when executed by the processor, cause the processor to synchronize with the marine electronics device.

10. The wearable device of claim 1, wherein the memory further comprises executable instructions which, when executed by the processor, cause the processor to transmit the record to the marine electronics device for display of the occurrence of the bite or the catch on a screen of the marine electronics device.

11. A non-transitory computer-readable medium having stored thereon a plurality of computer-executable instructions which, when executed by a computer, cause the computer to:
   receive motion data of an object used for fishing activities from one or more motion sensors of a wearable device, attached to the object, wherein the object is either an appendage of a user or a fishing rod such that motion of the object during the fishing activities defines one or more determinable patterns that are each associated with a corresponding fishing activity, wherein the one or more motion sensors are within the wearable device and not configured to directly attach to the appendage of the user or the fishing rod, wherein the wearable device and the one or more motion sensors are each not configured to attach to or interact with a fishing line;

analyze the motion data of the object to determine if the motion of the object defines at least one of the determinable patterns associated with a corresponding fishing activity, wherein the fishing activity includes at least one of occurrence of a cast, occurrence of a bite, or occurrence of a catch;

determine that the motion of the object defines at least one of the determinable patterns that corresponds to occurrence of a cast;

determine, based on the motion data of the object, a type of fishing cast by considering at least a basic fishing cast, a roll fishing cast, and a side fishing cast and choosing the type of fishing cast that corresponds to the motion data of the object, wherein the determination of the type of fishing cast is based on motion data that is based on motion of either the appendage of the user or the fishing rod and not direct motion of the fishing line;

determine a time associated with receipt of the motion data;

record the occurrence of the cast such that the determined type of fishing cast and determined time are associated with the occurrence of the cast; and wirelessly transmit the record of the associated occurrence of the cast, type of fishing cast, and time to a remote marine electronics device for further association with additional data, wherein the additional data includes a location that is recorded by the marine electronics device, and whereby the record of the occurrence of the cast, the type of cast, the time, and the location are stored in an associated manner in memory of the marine electronics device for operation by the marine electronics device that comprises combination with other fishing data by the marine electronics device to provide comprehensive fishing data of a fishing trip and display by a screen of the marine electronics device.

12. The non-transitory computer-readable medium of claim 11, wherein transmission of the recorded data occurs after determination of each occurrence of the cast.

13. The non-transitory computer-readable medium of claim 11, wherein the plurality of computer-executable instructions, when executed by the computer, further cause the computer to transmit the record to the marine electronics device for display of the occurrence of the cast on a screen of the marine electronics device.

14. The non-transitory computer-readable medium of claim 11, wherein the plurality of computer-executable instructions, when executed by the computer, further cause the computer to display the occurrence of the cast on a display of the wearable device.

15. A non-transitory computer-readable medium having stored thereon a plurality of computer-executable instructions which, when executed by a computer, cause the computer to:

receive motion data of an object used for fishing activities from one or more motion sensors located within a wearable device attached to the object, wherein the object is an appendage of a user such that motion of the object during the fishing activities defines one or more determinable patterns that are each associated with a corresponding fishing activity, wherein the wearable device is configured to attach to the appendage of the user, wherein the one or more motion sensors are within the wearable device and not configured to directly attach to the appendage of the user, and wherein the wearable device and the one or more motion sensors are each not configured to attach to or interact with a fishing line;

analyze the motion data of the object to determine if the motion of the object defines at least one of the determinable patterns associated with a corresponding fishing activity, wherein the fishing activity includes at least one of occurrence of a cast, occurrence of a bite, or occurrence of a catch;

determine, based on the motion data from the one or more motion sensors, that the motion of the object defines at least one of the determinable patterns that corresponds to either the occurrence of a catch or the occurrence of a bite, wherein the determinable patterns that correspond to either the occurrence of a bite or occurrence of a catch include motion data that is based on motion of the appendage of the user and not direct motion of the fishing line;

determine a time associated with receipt of the motion data;

record the occurrence of the catch or the bite such that the determined time is associated with the occurrence of the bite or the catch; and wirelessly transmit the record of the associated occurrence of the bite or the catch and time to a remote marine electronics device for further association with additional data, wherein the additional data includes a location that is recorded by the marine electronics device, and whereby the record of the occurrence of the bite or the catch, the time, and the location are stored in an associated manner in memory of the marine electronics device for operation by the marine electronics device that comprises combination with other fishing data by the marine electronics device to provide comprehensive fishing data of a fishing trip and display by a screen of the marine electronics device.

16. The non-transitory computer-readable medium of claim 15, wherein transmission of the recorded data occurs after determination of each occurrence of the catch or the bite.

17. The non-transitory computer-readable medium of claim 15, wherein the plurality of computer-executable instructions, when executed by the computer, further cause the computer to transmit the record to the marine electronics device for display of the occurrence of the bite or the catch on a screen of the marine electronics device.

18. The non-transitory computer-readable medium of claim 15, wherein the plurality of computer-executable instructions, when executed by the computer, further cause the computer to display the occurrence of the catch or the bite on a display of the wearable device.

19. A wearable device configured to be attached to an object used for fishing activities, the wearable device comprising:

a housing that is configured to attach to the object, wherein the housing includes:
at least one sensor configured to detect motion of the object, wherein the object is either an appendage of a user or a fishing rod such that motion of the object during the fishing activities defines one or more determinable patterns that are each associated with a corresponding fishing activity, wherein the at least one sensor is within the wearable device and not configured to directly attach to the appendage of the user or the fishing rod, wherein the wearable device and the at least one sensor are each not configured to attach to or interact with a fishing line; and a computer system having a processor and memory having stored thereon a plurality of executable instructions which, when executed by the processor, cause the processor to:
  receive motion data of the object from the at least one sensor;
  analyze the motion data of the object to determine if the motion of the object defines at least one of the determinable patterns associated with a corresponding fishing activity, wherein the fishing activity includes at least one of occurrence of a cast, occurrence of a bite, or occurrence of a catch;
  determine that the motion of the object defines at least one of the determinable patterns that corresponds to occurrence of a cast;
  determine, based on the motion data of the object, a type of fishing cast by considering at least a basic fishing cast, a roll fishing cast, and a side fishing cast and choosing the type of fishing cast that corresponds to the motion data of the object, wherein the determination of the type of fishing cast is based on motion data that is based on motion of either the appendage of the user or the fishing rod and not direct motion of the fishing line;
  determine a time associated with receipt of the motion data;
  record the occurrence of the cast such that the determined type of fishing cast and determined time are associated with the occurrence of the cast; and
  wirelessly transmit the record of the associated occurrence of the cast, type of fishing cast, and time to a remote marine electronics device for further association with additional data, wherein the additional data includes a location that is recorded by the marine electronics device, and whereby the record of the occurrence of the cast, the type of cast, the time, and the location are stored in an associated manner in memory of the marine electronics device for operation by the marine electronics device that comprises combination with other fishing data by the marine electronics device to provide comprehensive fishing data of a fishing trip and display by a screen of the marine electronics device.

20. The wearable device of claim 19, wherein the memory further comprises executable instructions which, when executed by the processor, cause the processor to transmit the record to the marine electronics device for display of the occurrence of the cast on a screen of the marine electronics device.

21. The wearable device of claim 19, wherein the memory further comprises executable instructions which, when executed by the processor, cause the processor to display the occurrence of the cast on a display of the wearable device.

22. A system for recording fishing statistics, the system comprising:
  a wearable device configured to be attached to an object used for fishing activities, the wearable device comprising:
    at least one sensor configured to detect motion of the object, wherein the object is an appendage of a user such that motion of the object during the fishing activities defines one or more determinable patterns that are each associated with a corresponding fishing activity, wherein the at least one sensor is within the wearable device and not configured to directly attach to the appendage of the user, wherein the wearable device and the at least one sensor are each not configured to attach to or interact with a fishing line; and
    a computer system having a wearable device processor and memory having stored thereon a plurality of executable instructions which, when executed by the wearable device processor of the wearable device, cause the wearable device processor to:
      receive motion data of the object from the at least one sensor;
      analyze the motion data of the object to determine if the motion of the object defines at least one of the determinable patterns associated with a corresponding fishing activity, wherein the fishing activity includes at least one of occurrence of a cast, occurrence of a bite, or occurrence of a catch;
      determine, based on the motion data from the at least one sensor, that the motion of the object defines at least one of the determinable patterns that corresponds to either the occurrence of a bite or occurrence of a catch, wherein the determinable patterns that correspond to either the occurrence of a bite or occurrence of a catch include motion data that is based on motion of the appendage of the user and not direct motion of the fishing line;
      determine a time associated with receipt of the motion data;
      record the occurrence of the bite or the catch such that the determined time is associated with the occurrence of the bite or the catch; and
      wirelessly transmit the record of the associated occurrence of the bite or the catch and time to a remote marine electronics device; and
  the marine electronic device comprising a marine electronic device processor and memory having stored thereon a plurality of executable instructions which, when executed by the marine electronic device processor of the marine electronic device, cause the marine electronic device processor to:
    receive the record of the occurrence of the catch or the bite;
    record, in response to receiving the record, a location; and
    store the record of the occurrence of the catch or the bite, the time, and the location in an associated manner in the memory of the marine electronics device for operation by the marine electronics device that comprises combination with other fishing data by the marine electronics device to provide comprehensive fishing data of a fishing trip and display by a screen of the marine electronics device.

23. The system of claim 22, wherein the wearable device comprises a screen, and wherein the plurality of executable instructions of the wearable device are further configured to cause the processor of the wearable device to display the occurrence of the catch or the bite on the screen of the wearable device.

24. The system of claim 22, wherein the marine electronics devices comprises a screen, and wherein the plurality of executable instructions of the marine electronics device are further configured to cause the processor of the marine electronics device to display the occurrence of the catch or the bite on the screen of the marine electronics device.

* * * * *